United States Patent [19]

Malcmacher et al.

[11] Patent Number: 4,878,842

[45] Date of Patent: Nov. 7, 1989

[54] APPARATUS AND METHOD FOR PREPARING TEETH FOR CROWN OR BRIDGE WORK OR OTHER DENTAL WORK

[76] Inventors: Louis J. Malcmacher, 30016 Donoit Rd., Westlake, Ohio 44145; Jeffrey S. Gross, 34586 Lakeshore Blvd., Eastlake, Ohio 44094

[21] Appl. No.: 115,704

[22] Filed: Nov. 2, 1987

[51] Int. Cl.⁴ .............................................. A61C 19/04
[52] U.S. Cl. ........................................ 433/72; 433/75; 433/102; 433/165; 433/215; 433/223
[58] Field of Search ...................... 433/72, 75, 76, 102, 433/165, 215, 223; 33/513, 514, 638

[56] References Cited

U.S. PATENT DOCUMENTS

| 447,475 | 3/1891 | Pomeroy | 33/201 |
|---|---|---|---|
| 3,388,473 | 6/1968 | Loran | 433/75 |
| 4,165,562 | 8/1979 | Sarfatti | 433/102 |
| 4,449,929 | 5/1984 | Reese | 433/72 |
| 4,509,268 | 4/1985 | Marquam et al. | 33/201 |
| 4,738,619 | 4/1988 | Ross | 433/72 |

FOREIGN PATENT DOCUMENTS 2746313  4/1979  Fed. Rep. of Germany ........ 433/75

OTHER PUBLICATIONS

"S. S. White Burns", No. 522, 2/1975.

Primary Examiner—John J. Wilson
Attorney, Agent, or Firm—Calfee, Halter & Griswold

[57] ABSTRACT

Selection of a proper drill bit for preparing a tooth to receive a crown or a bridge is accomplished through the use of a kit which includes a measuring guide and a template showing the profiles of various drill bits. The measuring guide and template are adapted to cooperate with the conventional X-ray. The X-ray is placed behind the measuring guide and oriented with the axis of the tooth perpendicular to a scale which is printed on the measuring guide. The measuring guide is otherwise transparent. By holding the X-ray and measuring guide up to light, a safe margin around the pulp chamber can be identified by the lines of the scale. Next, the drill template is placed in the measuring guide and manipulated until a drill bit profile is located which will maintain the safe margin around the pulp chamber and yet not cut into adjacent teeth. The method is taught together with a kit for practicing the method. The kit includes a selection of drill bits, the drill bit template, and measuring guide.

6 Claims, 2 Drawing Sheets

APPARATUS AND METHOD FOR PREPARING TEETH FOR CROWN OR BRIDGE WORK OR OTHER DENTAL WORK

BACKGROUND AND SUMMARY OF THE INVENTION

In preparing a tooth for the application of a crown or a bridge, it is necessary to remove portions of the tooth. Conventionally this is done by grinding or drilling. In removing this material, it is important to leave a stub of the tooth which is properly shaped to receive and support the crown or bridge, and at the same time it is essential not to invade the pulp cavity within the tooth. Further, for the convenience of both the doctor and patient it is important for the preparation to be performed as quickly as possible.

The present invention relates to an apparatus and method for drilling teeth, and particularly to an apparatus and method for simply and accurately determining an appropriate drill bit size and configuration for preparing a tooth for a crown or bridge.

The apparatus and method of the invention enables a dentist to determine quickly the appropriate drill bit for precise and efficient reduction of the tooth structure.

One aspect of the invention comprises the apparatus for drilling the tooth and determining the proper drill bit form for the particular tooth. The apparatus comprises a kit including special measuring guides (described more fully hereinafter) and a plurality of drill bits. The guides enable the dentist to determine the proper drill bit form, and the drill bits are proportioned to provide a system for properly drilling the teeth.

A specific aspect of the invention comprises a system for determining the proper drill bit to use for a given tooth. That structure comprises a pair of transparent sheets which are designed to provide visual information about a tooth and the drill bit most suited therefor. When superimposed on an X-ray of the tooth to be prepared, the transparent sheets can be used to determine the proper drill bit form for drilling the tooth.

Still further the invention comprises a method for selecting the proper drill bit for drilling or shaping a tooth. According to the method, an X-ray is provided of the tooth to be prepared, and a first measuring sheet is superimposed on the X-ray to provide a visual picture of the dimension of the tooth. A second transparent sheet or template carries the profiles of a selection of different drill bits. When the template is superimposed on the first sheet, it provides a visual impression of the amount of tooth material each bit would remove if used on the selected tooth. The proper bit is the one which will in a single pass remove the desired amount of tooth while leaving a safe margin surrounding the pulp cavity and without cutting into neighboring teeth.

These and other features of the present invention will become clear from the following specification when taken together with the accompanying drawings.

DETAILED DESCRIPTION OF PREFERRED EMBODIMENTS

Figure 1:
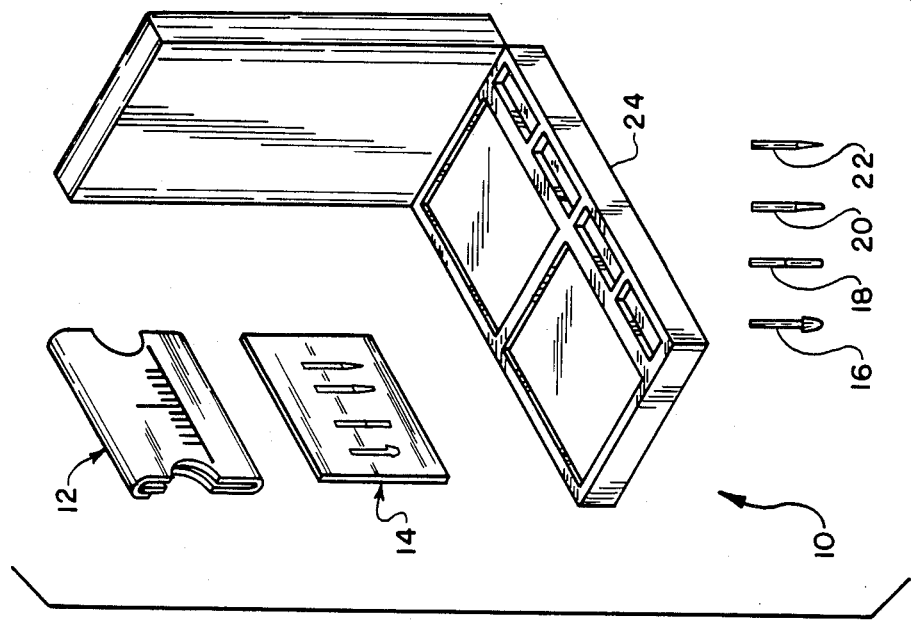
FIG. 1 illustrates a kit assembled according to the present invention providing a selection of drill bits, a measuring guide, a transparent template of the drill bits, and a convenient storage case.
Figure 5:
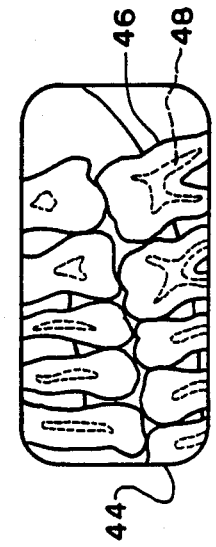
FIG. 5 is an illustration of a representative dental X-ray showing teeth with their pulp cavities in phantom.

FIG. 1 illustrates a kit 10 for use in selecting an appropriate and efficient drill bit for preparing a tooth for a crown or bridge. Kit 10 includes a measuring guide 12, a drill template or guide 14, a selection of drill bits 16, 18, 20, and 22, and a convenient carrying case 24. The bits 16–22 have varying profiles and diameters and may be faced with diamond or another hard, abrasive material. When performing interproximal reduction or reduction of the facial or lingual tooth surfaces, the dentist positions the bit tangent to the tooth surface to be reduced. Therefore the amount of reduction is equal to the diameter of the bit, and the shape of the curved tooth surface connecting the reduced tooth surface with original tooth enamel is directly related to the shape of the drill bit.

Figure 2:
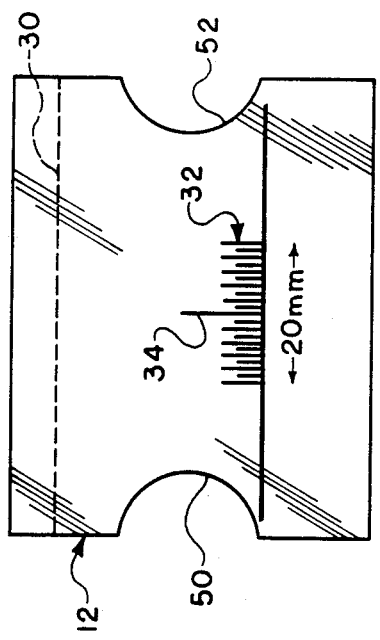
FIG. 2 is a front view of the measuring guide of FIG. 1.
Figure 3:
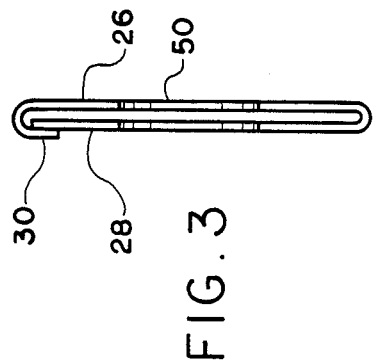
FIG. 3 shows an end view of the measuring guide of FIG. 1.

The measuring guide 12 and drill template 14 are both formed of transparent plastic. The guide 12 (FIGS. 2 and 3) is formed from a single sheet of plastic folded to form front panel 26, rear panel 28, and a flap 30 folded over the top. The front panel 26 includes a scale 32 (FIG. 2) which may be conveniently formed of twenty parallel lines spaced one millimeter apart. A central scribe line 34 is positioned midway along the length of the scale and is longer than the other lines of the scale 32 so that it is readily distinguishable from them. The lines forming the scale 32 extend perpendicular to the folds which define the front and rear panels 26 and 28 and the flap 30.

The drill template 14 is formed of a transparent plastic panel which is proportioned to slide between the front and rear panels 26 and 28 of the measuring guide 12. The drill template 14 includes full scale outlines 36, 38, 40 and 42 of drill bits 16, 18, 20, and 22 as well as their identifying part numbers. The part numbers facilitate reordering bits when necessary.

Figure 6:
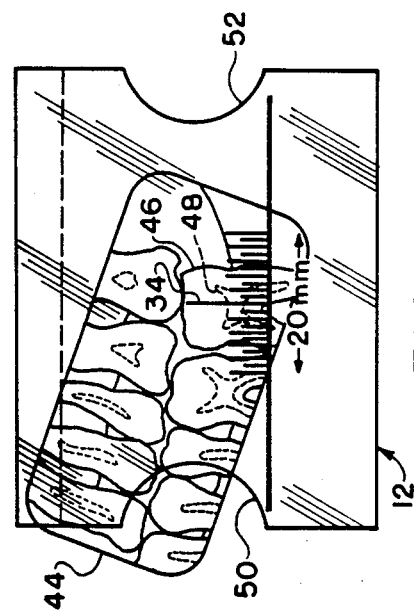
FIG. 6 shows the measuring guide of FIG. 2 superimposed on the X-ray of FIG. 5.

To use the kit 10, the dentist prepares a conventional X-ray 44 of the tooth 46 which is to be prepared for a crown or bridge. The X-ray 44 shows the pulp chamber 48 as well as the general outline of the tooth 46 and its neighbors. The X-ray 44 is then placed behind the panel 28 of the measuring guide 12 and positioned so that the central scribe line 34 approximately bisects the pulp chamber 48 (see FIG. 6).

By placing the X-ray behind the scale 32 the dentist is easily able to identify a safe margin around the pulp chamber. This margin, as is conventional, varies from one millimeter to two millimeters depending upon the particular tooth. The selection of the appropriate margin is made according to the professional judgment of the dentist.

Figure 7:
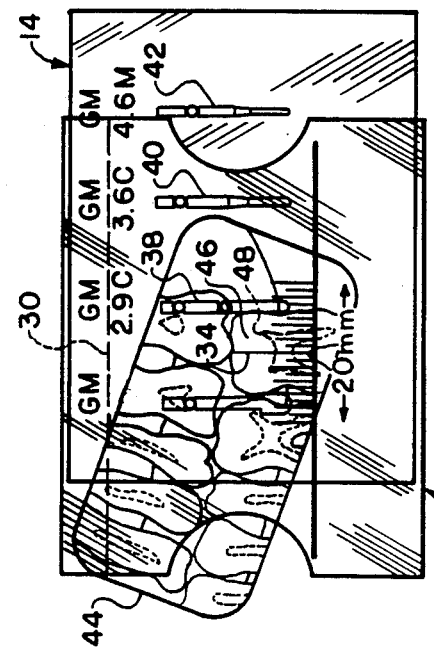
FIG. 7 shows the transparent drill template of FIG. 4 superimposed on the X-ray and measuring guide of FIG. 6.
Figure 4:
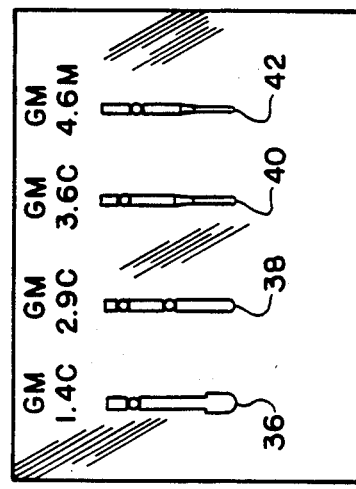
FIG. 4 is a front view of the transparent template of FIG. 1.

In order to select a drill bit from the bits 16–22, the dentist places the drill template 14 between the front and rear panel 26 and 28 of the measuring guide 12 (see FIG. 7). The drill template 14 is then superimposed on the tooth to be prepared. Manipulation of the drill template 14 between the front and rear panels 26 and 28 is facilitated by the arcuate cut-outs 50 and 52 which are formed in opposite lateral edges of the guide 12. Once properly positioned, the drill template 14 is held in place by friction between the front and rear panels 26 and 28 and by gripping the measuring guide 12 between thumb and forefinger to squeeze the front and rear panels against the drill template.

The correct drill bit is the one whose outline does not overlap either the adjacent tooth (which is not to be cut into) or the scale line identifying an appropriate safe margin. By maneuvering the drill template, the dentist is able to obtain quickly and easily a visual impression of the results of selecting any particular drill bit. When the drill bit which produces the desired safety margin has been identified, the dentist uses it to reduce the tooth in a conventional manner.

The present invention may also be used to select the proper drill bit for other tooth preparations. For example, when selecting the proper bit to drill a cavity in preparation for a filling, the X-ray 44 may be oriented so that the scale 32 measures downward from the tooth crown toward the pulp chamber. The scale then serves to assist in selecting a bit of the proper length to assure that a proper margin is maintained above the pulp chamber. The same drill template 14 could be used for this purpose, or a different drill template having the outlines of bits of varying lengths could be provided. It is also possible to provide the guide 12 with a scale perpendicular to the scale 32 for providing a visual image of the effect of selecting a particular drill bit. No matter what the orientation of the scale 32, its effect is to enable the dentist to identify a safe margin in tooth preparation, and the drill template 14 shows the dentist what a particular drill bit will do.

Thus the present invention provides a method and apparatus for quickly and easily selecting an appropriate drill bit for tooth reduction or other tooth preparation. The apparatus includes the kit 10 including measuring guide 12, drill template 14 and a selection of drill bits 16-22 with varying profiles. Using the guide 12 and template 14 in conjunction with the patient's X-ray 44, facilitates selection of the proper one of the drill bits 16-22.

What is claimed is:

1. A dental drilling kit comprising a plurality of drill bits of different profiles and measuring means for determining the proper one of the bits for use in preparing a tooth, said measuring means comprising a first transparent sheet having a reference scale printed on it and a second reference sheet having a profile of each of the drill bits printed on it, said first sheet formed of a transparent plastic material folded to define a front panel and a rear panel, said front panel and said rear panel being adapted to receive said second reference sheet therebetween, said front and rear panels including congruent arcuate cut-outs in opposite lateral edges to facilitate manipulation of said second reference sheet between said front panel and said rear panel.

2. A method of selecting a drill bit for reducing a patient's tooth said method comprising the steps of
   providing an X-ray of the tooth to be prepared and surrounding teeth, if any, the X-ray showing the outline of the pulp chamber of the tooth to be prepared,
   superimposing a reference scale on the X-ray,
   using the reference scale to identify a safe margin around the pulp chamber of the tooth to be prepared, and
   superimposing a drill bit profile on the X-ray and scale, the drill bit profile demonstrating that a drill bit having the profile will provide adequate clearance for the pulp chamber and will not contact adjacent teeth.

3. The method of claim 2 wherein the step of superimposing a drill bit profile includes the step of superimposing a sheet with a plurality of drill bit profiles and manipulating the sheet to selectively position one of the drill bit profiles over the portion of the selected tooth which is to be reduced.

4. The method of claim 2 wherein the step of superimposing a reference scale includes the step of positioning a reference scale with its mid-line approximately centered on the pulp chamber of the tooth to be reduced.

5. The method of claim 2 wherein the step of superimposing a sheet with a plurality of drill bit profiles includes the step of inserting the sheet with a plurality of drill bit profiles between the front and rear panels of a transparent sheet on which the reference scale is printed.

6. The method of claim 5 wherein the step of superimposing a reference scale on the X-ray includes the step of placing the X-ray behind the rear panel of a transparent sheet having front and rear panels, the reference scale being printed on the front panel thereof.

* * * * *